United States Patent
Lodwig (10) Patent No.: US 9,232,913 B2
(45) Date of Patent: Jan. 12, 2016

(54) METHOD AND APPARATUS FOR MEASURING DISTORTION PRODUCT OTOACOUSTIC EMISSIONS (DPOAE) BY MEANS OF FREQUENCY MODULATED STIMULI

(71) Applicant: Andre Lodwig, Worthsee (DE)

(72) Inventor: Andre Lodwig, Worthsee (DE)

(73) Assignee: Path Medical GMBH, Germering (DE)

(*) Notice: Subject to any disclaimer, the term of this patent is extended or adjusted under 35 U.S.C. 154(b) by 270 days.

(21) Appl. No.: 13/657,158

(22) Filed: Oct. 22, 2012

(65) Prior Publication Data
US 2014/0114209 A1    Apr. 24, 2014

(51) Int. Cl.
*A61B 5/12* (2006.01)
*A61B 5/00* (2006.01)

(52) U.S. Cl.
CPC ............ *A61B 5/125* (2013.01); *A61B 5/7203* (2013.01); *A61B 5/7228* (2013.01)

(58) Field of Classification Search
CPC ........................................................ A61B 5/12
USPC ........................................... 600/559; 73/585
See application file for complete search history.

(56) References Cited

U.S. PATENT DOCUMENTS 5,601,091 A * 2/1997 Dolphin .................... 600/559
6,463,411 B1 * 10/2002 Li et al. .................... 704/226
7,223,245 B2 * 5/2007 Zoth et al. ................. 600/559

OTHER PUBLICATIONS

James, A., Mount, R., & Harrison, R. (2002). Contralateral suppression of DPOAE measured in real time. Clinical Otolaryngology & Allied Sciences, 27(2), 106-112. doi:10.1046/j.1365-2273.2002.00541.x.*
Scholz, Gunther, Hirschfelder, Anke, Marquardt, Johannes Hensel, Mrowinski, Dieter. (Jan. 2, 1999). Low-frequency Modulation of the 2f1-f2 distortion product otoacoustic emissions in the human ear. Hearing Research, 130(1999), 189-196.*
Dimitrijevic, Andrew, Michalweski, Henry J., Zeng, Fan-Gang, Pratt, Hillel, Starr, Arnold. (2008) Frequency Changes in a Continuous Tone: Auditory Cortical Potentials. Clinical Neurophysiology, (119) (2008), 2111-2124.*
Arnold, David J., Lonsbury-Martin, Brenda, Martin, Glen K. (Feb. 1999). High-Frequency Hearing Influences Lower-Frequency Distortion-Product Otoacoustic Emissions. Arch Otolaryngol Head Neck Surg, (125)(2) (1999), 215-222.*
Summit Dhar, Separation Anxiety: DPOAE Components Refuse to be Separated, http://www.otoemissions.org/guest_editorials/2009/dhar_2009.htm.
Xiao-Ming, "Distortion product otoacoustic emission fine structure is responsible for variability of distortion product otoacoustic emission contralateral suppression", J. Acoust Soc. Am., Jun. 2008 123(6): 4310-20.

* cited by examiner

*Primary Examiner* — Adam J Eiseman
*Assistant Examiner* — Yasmeen S Warsi
(74) *Attorney, Agent, or Firm* — Marcus G. Theodore (57) ABSTRACT

A method to reduce DPOAE fine structure in the measurement of DPOAE acoustic signals generated in the cochlea in response to two primary tones.

21 Claims, 10 Drawing Sheets

METHOD AND APPARATUS FOR MEASURING DISTORTION PRODUCT OTOACOUSTIC EMISSIONS (DPOAE) BY MEANS OF FREQUENCY MODULATED STIMULI

BACKGROUND OF THE INVENTION

1. Field

This invention relates to measurement of Distortion Product Otoacoustic Emissions (DPOAE), acoustic signals generated in the cochlea. In particular, it relates to a method to reduce DPOAE fine structure by using frequency modulated primary tones.

2. State of the Art

The mammal and human ear features an amplification system, which amplifies soft sound by up to 40 dB. This "cochlear amplifier" employs so-called outer hair cells (OHC) located in the organ of Corti in the inner ear. The mechanical activity of the OHC is non-linear, causing non-linear distortion to be produced in the inner ear.

The non-linearity of the ear has been known over a century, but it was relatively recent that the OHC of the cochlea were identified as the primary cause. The middle ear is quite linear over sound pressures of 40 to 110 dB SPL, and does not result in noticeable distortion at normal listening levels. The inner ear non-linearity does produce distortion, which can be heard, and measured in the ear canal. Measurement of distortion products in the ear canal is used as a hearing test for newborn infants, since the distortion products are absent for certain forms of hearing impairment.

In principle the ear non-linearity could be expressed as a power series; that is, where the response is linearly proportional to the sound pressure, plus a term proportional to the square of the sound pressure, cube of the pressure, etc. If two frequencies were present, a square term would produce intermodulation products equal to the sum and difference of the two frequencies. A cubic term would produce products equal to twice one frequency plus and minus the other frequency.

If continuous sinusoidal sounds are applied as a stimulus, the sound response generated by the inner ear can be separated from the stimulus by analysing the outside sound response generated frequencies of the stimuli. Since intermodulation products of the primary frequencies are generated as a result of the non-linearity of the functioning inner ear, the presence of signals whose frequencies do not match ("clash") with the stimulus signals is a deciding factor in proving the integrity of the inner ear. These signals are termed distortion product otoacoustic emissions (DPOAE).

DPOAE are acoustic signals, generated in the cochlea of mammals, especially humans, as a response of two sine tones of different frequency ("primary tones") used as stimuli. The probe for recording DPOAE typically contains two loudspeakers for stimulation and one or more microphones for recording.

Typically, primary tones with levels $L_1$, $L_2$ and frequencies $f_2$ are set with $f_1 < f_2$ and $L_1 \geq L_2$ and the frequency ratio $f_2/f_1$ is in the order of 1.2 to 1.3.

The strongest DPOAE component is generated at $f_{DPOAE} = 2*f_1 - f_2$. This component is the one used by virtually all commercial DPOAE equipment.

DPOAE measurements work in a broad frequency range, from less then 500 Hz to more than 10 kHz, depending on the subject, recording equipment, and noise conditions.

DPOAE are thought to be generated by the so-called "outer hair cells", which act as an acoustic amplifier in the cochlea.

Since the DPOAE are only a side effect of this cochlear amplifier, the signal that can be recorded in the ear canal is normally small in amplitude, compared to background noise and stimuli. This makes signal processing necessary to detect the signal combined with background noise.

DPOAE Detection

The common method to detect DPOAE is framing the measurement of raw data in frames of constant length, with all frequencies ($f_1$, $f_2$, $f_{DPOAE}$ being multiples of the frame rate).

The frames or the FFT components of the frames are usually averaged with some artifact rejection scheme to finally decide a DPOAE has been found or to determine its amplitude.

A widely used method to decide a DPOAE has been recorded is to observe the amplitude of the recorded spectrum at $f_{DPOAE}$ compared to the neighboring frequency components ("SNR criterion").

In order to support the stimuli described below, DPOAE detection needs to be designed differently, to allow small, continuous frequency deviations.

DPOAE Fine Structure

When measuring DPOAE with a high frequency resolution, such as one measurement every 20 Hz, fine structure can be observed in most subjects. Fine structure in this context means, that the amplitude of DPOAE varies with frequency, and can show variations of up to 20 dB within as little as 100 Hz primary tone frequency modification. This fine structure is thought to be the result of outer hair cells in the regions that are tuned to the DPOAE frequency that generate otoacoustic emissions (OAE) themselves, which can constructively or destructively interfere with the original source, located at the overlap region of the primary tones $f_1$ and $f_2$.

The main aspects of DPOAE fine structure are outlined in the article, "Separation Anxiety: DPOAE Components Refuse to be Apart", by Sumit Dhar, www.otoemissions.org/guest_editorials/2009/dhar/2009.htm.

Figure 1:
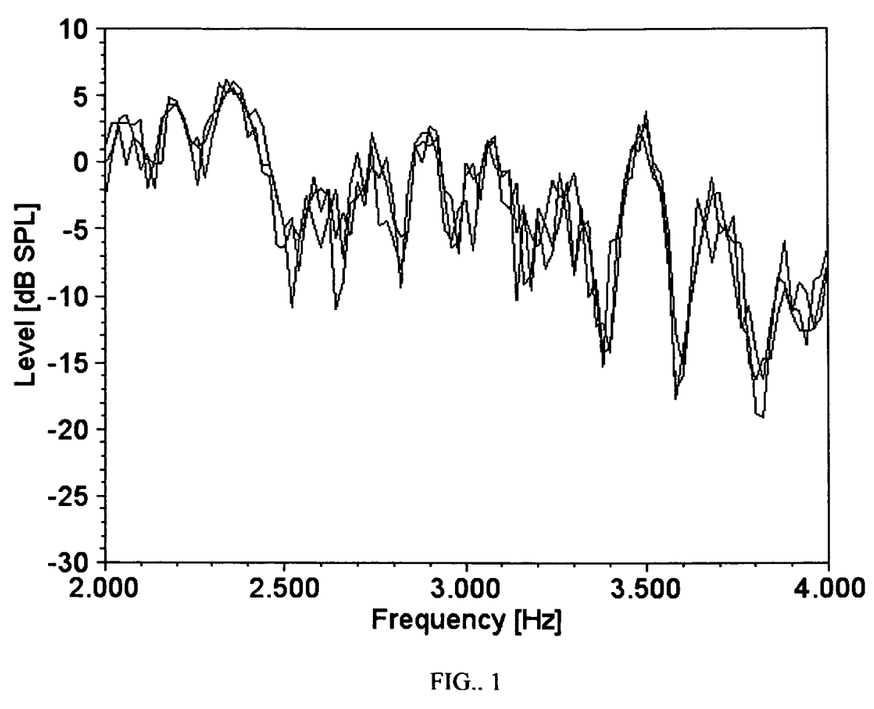
FIG. 1 is a graph of three recordings performed to prove the reproducibility of the fine structure.

An example of such a recording, ranging from 2 kHz to 4 kHz with 20 Hz resolution, is shown in FIG. 1. Three recordings were performed to prove the reproducibility of the fine structure.

DPOAE fine structure is unwanted in many applications of DPOAE measurements. In newborn hearing screening, test time is crucial. Hitting a fine structure minimum with one or more of the test frequencies can extend test time dramatically, or lead to refer results. Typically 4 to 6 frequencies are tested, with an "overall criterion" that passes a subject if, for example, DPOAE are found at 3 of the 4 frequencies.

When using DPOAE to estimate the hearing threshold, usually by extrapolating input-output functions, the fine structure, because it is level dependent, can severely corrupt the growth behavior at certain frequencies. This leads to large errors in estimating the hearing threshold.

In both cases, there is no need to measure exactly using only nominal stimulus frequencies. Deviations in the order of +100 Hz are tolerable for most applications. This is supported by the common DPOAE model, which predicts a certain region of the cochlea producing the DPOAE response. This region is thought to be close to the location tuned to $f_2$, and covers a frequency range anyway.

In many applications, it is even desirable to cover a frequency band with a single DPOAE measurement instead of a single frequency, since often only a few tests at selected frequencies can be done in reasonable time, which are then used to characterize performance of hearing over the complete frequency range. Typically, test frequencies are spaced as coarse as octaves of half-octaves.

In order to overcome unwanted effects of the DPOAE fine structure, it is desirable to disable or attenuate the so-called second source. Methods have been suggested to mask the second source with additional stimulus tones, for example a tone that is close to $f_{DPOAE}$.

However, these methods do not perform as stable as desired, and useful parameter settings vary strongly among subjects. The method described below provides a new approach for measuring DPOAE.

SUMMARY OF THE INVENTION

Frequency Modulated Stimuli

The invention comprises a method for measuring DPOAE by means of frequency-modulated stimuli that compensate for the fine structure effects, hereinafter referred to as FMD-POAE. The method for measuring DPOAE by means of frequency modulated stimuli comprises exposing a subject to an incoming signal comprised of two primary tones to elicit DPOAE responses, which are then recorded. The modified stimulus (FM modulated primary tones) makes the inner ear "produce" DPOAE without fine structure. That means the fine structure is not suppressed at the recoding part of the system, but at the generator (the cochlea) itself. Hence, statistics are not part of an artefact rejection scheme to reject or influence unwanted fine structure. Instead, the fine structure is avoided by use of modified stimulus.

DPOAE fine structure is also reported to interfere with the measurement of DPOAE suppression when applying contralateral masking, www.ncbi.nlm.nig.gov/pubmed/18537382. The use of frequency-modulated stimuli can reduce this effect and therefore allow better accuracy and reproducibility of such measurements. That is, if you apply masking sound to the left ear and look for level changes of the DPOAE in the right ear, or vice versa.

To detect the frequency modulated DPOAE signals, various analytical methods, such as quadrature demodulation can be used. Quadrature demodulation makes use of Cartesian coordinates, x and y. When considering quadrature modulation, the x-axis is called the I (in-phase) axis, and the y-axis is called the Q (quadrature) axis.

At least one of the primary tones is modulated in frequency, generally resulting in a frequency modulated DPOAE signal.

The method of measuring DPOAE is particularly used for newborn hearing screening where the patient does not understand how to respond to the stimuli. It is also used for diagnostic DPOAE measurements.

The statistical methodology used to reject environmental noise artifacts comprises weighted averaging, one-tailed, two-tailed, and hypothesis testing, or other suitable analytical methods.

One preferred method for measuring DPOAE includes calculating the I and Q components of the quadrature signal by multiplying the incoming (raw or pre-filtered) signal with appropriate sine and cosine functions. This method is also referred to as quadrature demodulation. The I and Q data is then independently windowed and framed before averaging the I and Q signals. The averaged I/Q vector is then statistically evaluated to detect a statistically significant DPAOAE signal and/or estimate its amplitude.

There are two possible explanations of how this can reduce fine structure. One explanation is that the DPOAE output of neighboring frequencies are just "averaged" by shifting forth and back the stimulus frequencies. A different explanation is that the Second source may be too slow to follow the constantly changing $f_{DPOAE}$.

The frequency modulation itself can be done in many different schemes, which will perform differently in achieving the goal of suppressing the Second source without reducing the DPOAE output of the First source too much.

Special attention has to be taken to the phase of the DPOAE signal, which can hinder a proper averaging or similar signal detection scheme. The detection algorithm needs to be "aware" of the current expected phase of the DPOAE response to make sure the signal is detected correctly.

One modulation scheme would be to shift both primary tones by a time-varying frequency shift, which would shift $f_{DPOAE}$ by the same absolute amount:

$$f_1 = f_{1BASE} + f(t)$$

$$f_2 = f_{2BASE} + f(t)$$

$$f_{DPOAE} = f_{DPOAE\_BASE} + f(t) \quad \text{(equation 1)}$$

where $f_{DPOAE} = 2*f_1 - f_2$ and f(t) being a modulation function, representing the frequency shift over time.

A different approach would be to shift f1 and f2 by a time varying factor:

$$f_1 = f_{1BASE} * f(t)$$

$$f_2 = f_{2BASE} * f(t)$$

$$f_{DPOAE} = f_{DPOAE\_BASE} * f(t) \quad \text{(equation 2)}$$

where f(t) is the modulation function, usually varying closely around 1.

Other paradigms are possible with the same effect, including paradigms that leave one of the primary tones unchanged.

A more general formula would be $$f_1 = f_{1BASE} + f_1(t)$$

$$f_2 = f_{2BASE} + f_2(t)$$

$$f_{DPOAE} = f_{DPOAE\_BASE} + f(t)$$

with $f(t) = 2*f_1(t) - f_2(t)$.

Careful selection of the modulation functions can help optimize the phase behavior of the DPOAE response to allow its proper detection. If $f_2(t) = 2*f_1(t)$, f(t)=0, which is a special case in that the DPOAE response is not modulated at all.

Figure 2:
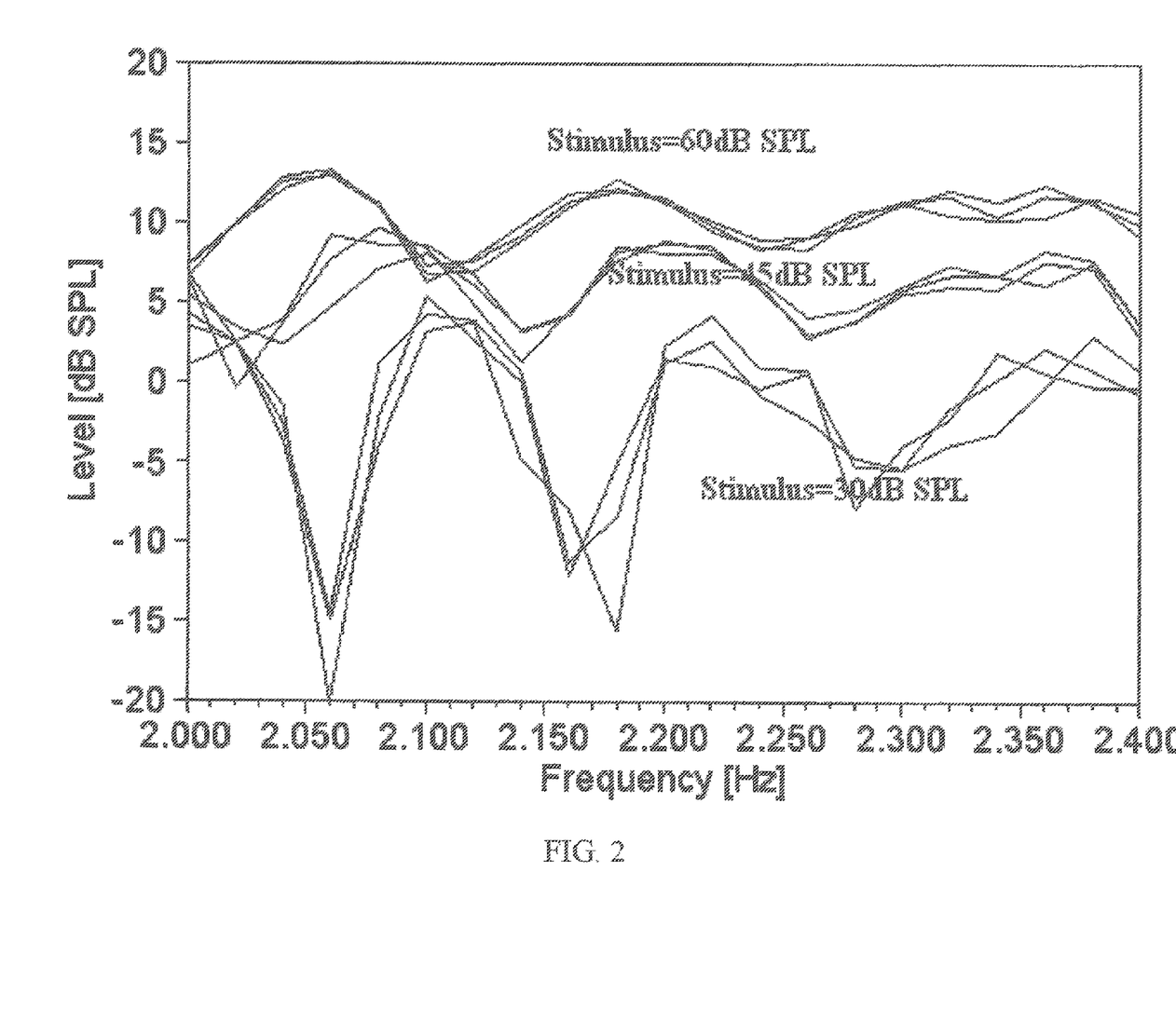
FIG. 2 is a graph of a recording showing the standard recording techniques for 3 stimulus levels and 3 recordings per setting.
Figure 2A:
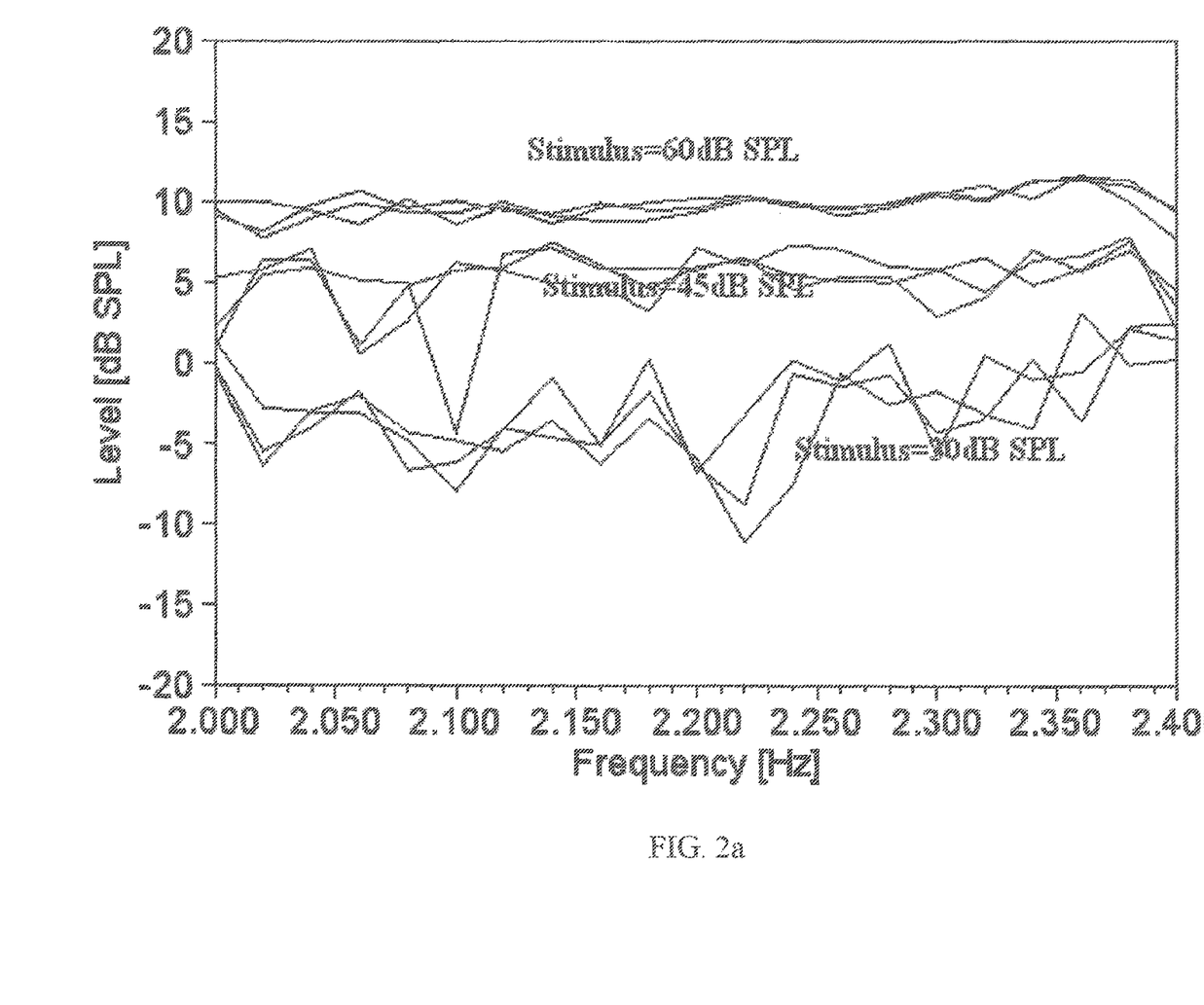
FIG. 2a is a graph of a recording showing FMDPOAE demonstrating the suppression of fine structure for 3 stimulus levels and 3 recordings per setting.

Experiments indicate that a sine- or triangle modulation with about ±100 Hz frequency shift at 1 Hz modulation rate results in a significant reduction of the fine structure in medium frequencies (2 kHz to 5 kHz). In lower and higher frequencies, parameters can be modified slightly for best performance. FIGS. 2, 2a show such a recording. The standard recording technique for 3 stimulus levels and 3 recordings per setting is shown in FIG. 2 and the FMDPOAE is shown in FIG. 2a.

Recording Technique

The common method to detect DPOAE is framing the measurement raw data in frames of constant length, with all frequencies ($f_1$, $f_2$, $f_{DPOAE}$ being multiples of the frame rate).

Repeating Discrete Fourier Transform (DFT) is then applied to the framed audio data, resulting in a spectrum representation of the data. Frame sizes are normally set to powers of 2, to apply a special implementation of the DFT, called Fast Fourier Transform (FFT).

The frames or the FFT components of the frames are usually averaged with some artifact rejection scheme to finally decide if a DPOAE has been found or to determine its amplitude. Alternatively, the frames can be averaged in time domain and the FFT performed on the averaged result with the same result.

Since the primary tone frequencies are picked to be multiples of the frame rates, they and the resulting DPOAE are located at fixed bins of the FFT results (spectra). The bin size of the FFT result is equal to the frame rate, with typical values being in the order of 20 to 50 Hz.

Assuming a frame size of 1,024 samples (a common choice because most FFT algorithms in use for sound processing require a number of samples be a power of two) gives 512 frequency bands. If we assume a sample rate of 44.1 kHz, we have a frequency range of 0 kHz to 22.05 kHz. (Nyquist theorem is two times the bandwidth of a bandlimited signal or a bandlimited channel). The width of each of our frequency bins, which is equal to the frame rate, is determined by the following formula:

bin width=frame rate=Nyquist frequency/number of bins;

giving a bin width of about 43 Hz.

To allow FM modulation of the signal components, this standard method cannot be used directly. One simple way to do so is to apply frequency modulation to the sampling frequency of the AD-DA converter. Some AD-DA converter chips provide such a feature. However, this would be limited to a modulation as described in equation 2, since all frequencies would be shifted with a common factor.

A more universal modulation range can be achieved if the frequencies are no longer multiples of the frame rates.

This can be achieved with a principle widely used in information technology, called quadrature demodulation or I/Q demodulation.

Figure 8:
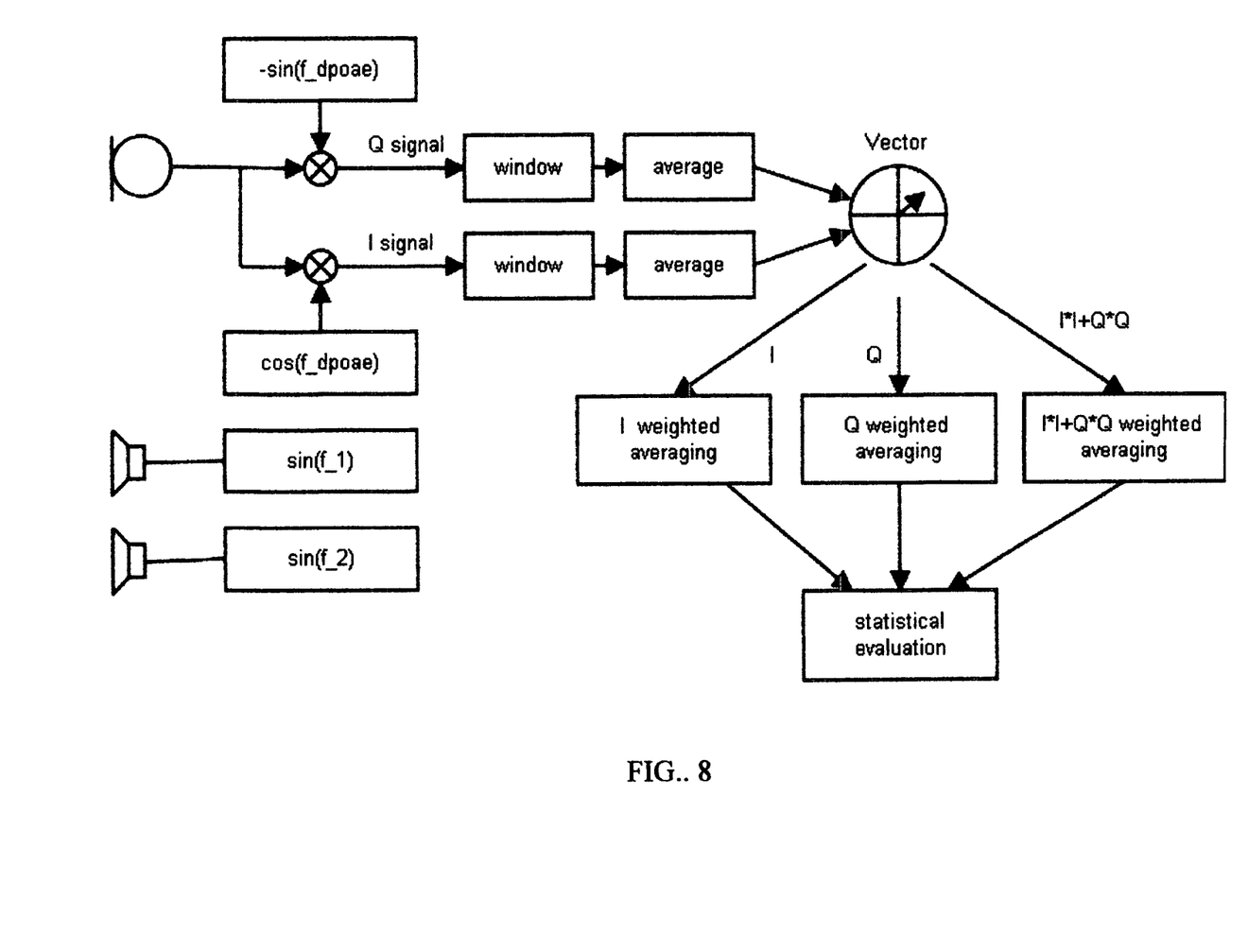
FIG. 8 is a schematic of the incoming signal sample per sample multiplied with sine and cosine of the known $f_{DPOAE}$.

FIG. 8 is a schematic of one example of how the incoming signal is sample per sample multiplied with sine and cosine of the known $f_{DPOAE}$, resulting in two so-called base band signals (I and Q signals).

These base band signals can then be windowed, framed, and averaged to collect the DPOAE signal, represented as a vector in the I/Q plane. Known statistical methods are then applied to decide if a valid response was detected. Artifact rejection schemes, such as weighted averaging, can also be applied to this scheme.

The "I" and "Q" signals are windowed, for example with a "raised cosine window" (see de.wikipedia.org/wiki/Raised-Cosine-Filter). For each resulting frame, the "I" and "Q" signal is averaged, resulting in a vector for each frame. A frame would typically cover 2048 to 4096 samples of data. With a sampling rate of 48 kHz, we would get about 25 new vectors per second.

Over frames, the resulting I and Q value for each vector, and $I^2+Q^2$ are averaged. This averaging can optionally be done with a weighting factor that is set lower if much noise is found in a frame and higher if less noise is found. A possible noise estimator would be the amplitude result of band pass filtering the raw data of each frame with a band pass that is centered at $f_{DPOAE}$.

The results of this averaging are called $I_{avg}$, $Q_{avg}$ and $P_{avg}$ here.

For a statistical evaluation, the averaged values can be evaluated, by calculating $C=\mathrm{sqrt}(I_{avg}^2+Q_{avg}^2)/\mathrm{sqrt}(P_{avg})$.

This C value can be compared to a given criterion, and if it exceeds a value of, for example 4, a DPOAE is detected.

Other statistical methods could also be applied to the general signal flow.

This recording and evaluation scheme works with any selection of $f_1$, $f_2$, and resulting $f_{DPOAE}$, including FM modulation schemes as described above. The frequencies do not need to be multiples of the frame rate and can be selected to any needed precision, independent of sampling rate and frame size.

Although the described method is primarily directed to a method for measuring DPOAE with frequency modulated primary tones used for the suppression of fine structure, it may also be used in conjunction with the performance of other hearing testing, measurements, and analysis where suppression of the fine structure is advantageous.

The method and apparatus described thus provides a new approach for measuring DPOAE.

DESCRIPTION OF THE ILLUSTRATED EMBODIMENTS

FIG. 1 is a graph of three recordings performed to prove the reproducibility of the fine structure.

FIG. 2 is a graph of a recording showing the standard recording techniques for 3 stimulus levels and 3 recordings per setting.

FIG. 2a is a graph of a recording showing FMDPOAE demonstrating the suppression of fine structure for 3 stimulus levels and 3 recordings per setting.

Figure 3:
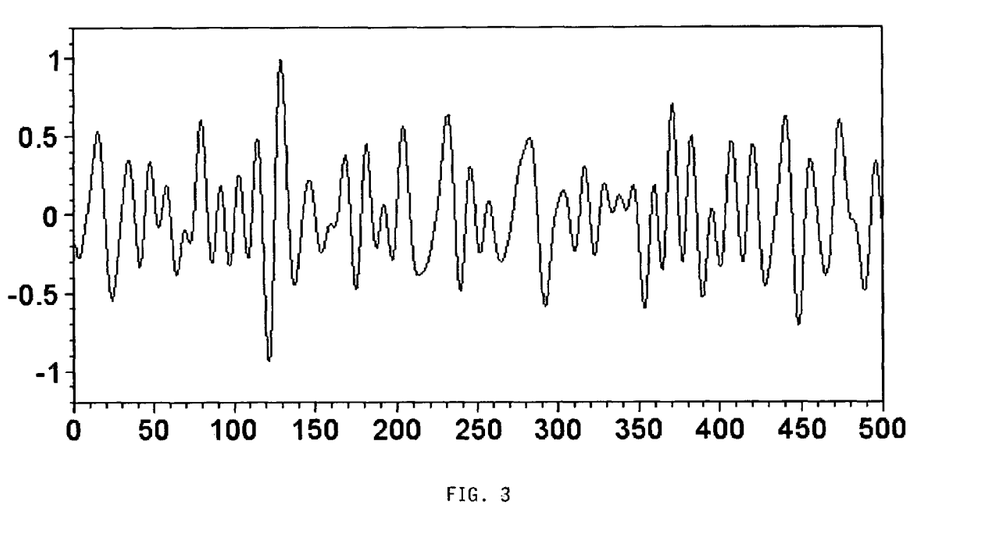
FIG. 3 illustrates a graph of a periodic function, f(t).

FIGS. 3 through 7 illustrate the FFT steps. FIG. 3 illustrates a graph of a periodic function, f(t).

Figure 4:
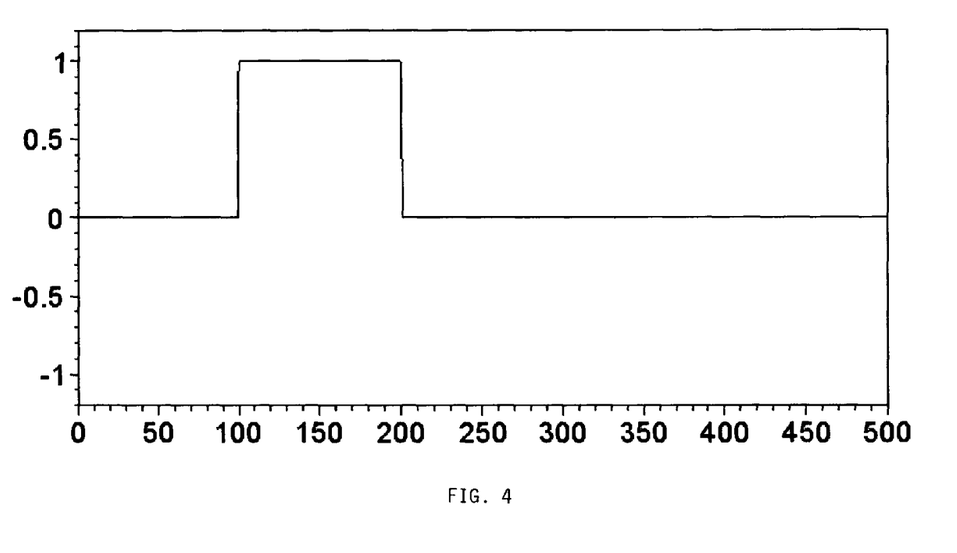
FIG. 4 is a graph of the window function w(t).

FIG. 4 is a graph of the window function w(t).

Figure 5:
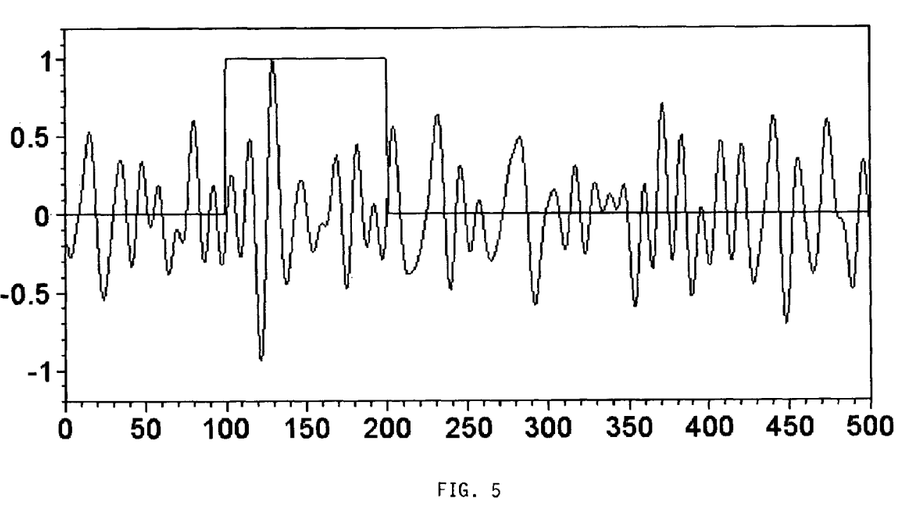
FIG. 5 is a plot of both the window function, w(t) and function ƒ(t)

FIG. 5 is a plot of both the window function, w(t) and function ƒ(t)

Figure 6:
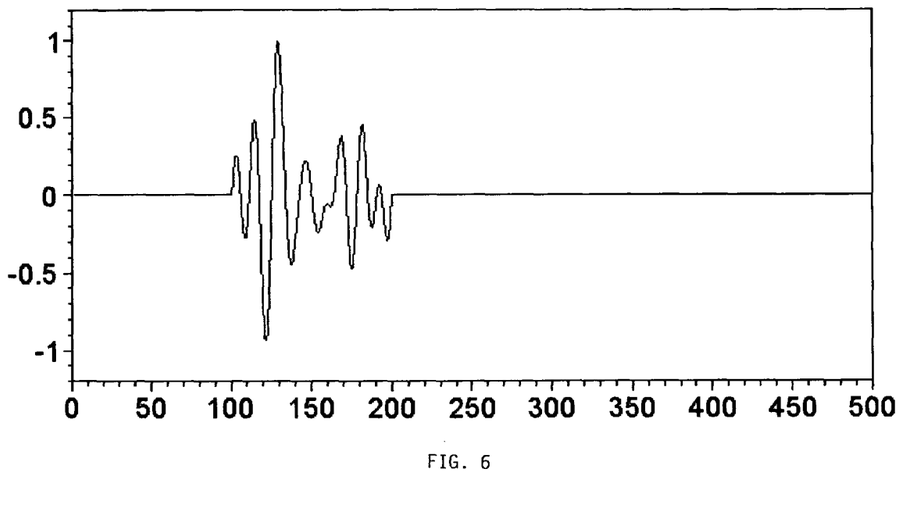
FIG. 6 is a plot of ƒ(t)*w(t).

FIG. 6 is a plot of ƒ(t)*w(t).

Figure 7:
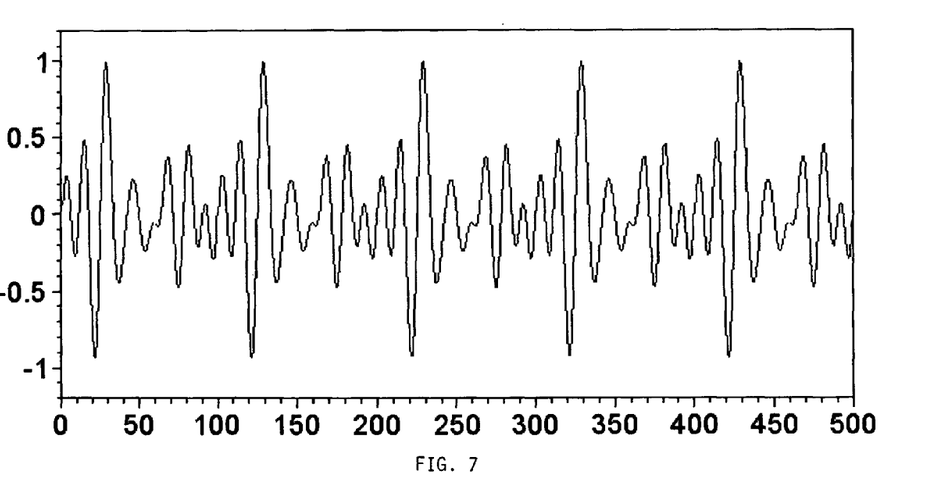
FIG. 7 is a periodicized segment periodically extending the windowed function, ƒ(t)*w(t), all along the t-axis.

FIG. 7 is a periodicized segment periodically extending the windowed function, ƒ(t)*w(t), all along the t-axis.

FIG. 8 is a schematic of the incoming signal sample per sample multiplied with sine and cosine of the known $f_{DPOAE}$. The common method to detect DPOAE is framing the measurement raw data in frames of constant length, with all frequencies ($f_1$, $f_2$, and $f_{DPOAE}$ being multiples of the frame rates.

The decoding part basically uses the same signal-theory as quadrature detection. In signal theory, one can "mix down" a signal from some carrier frequency to a different one. Radios do so, for example a FM tuner "mixes down" the stations RF signal at around 100 MHz to the so-called IF at 10.7 MHz. This makes filtering and amplifying much easier, because it only needs to be done at the lower and constant 10.7 MHz.

Mixing in this context basically means to multiply the signal with a sine signal. In the example of the radio, a "local oscillator" is used, in our example it would generate 110.7 MHz (just 10.7 MHz above the station we want to receive). The incoming, pre-filtered antenna signal would be multiplied with this local oscillator signal, and the station we want to receive would end up as a 10.7 MHz IF signal for filtering and amplification. In Radio reception, this is also referred to as "heterodyne" principle. (See en.wikipedia.org/wiki/Heterodyn)

Heterodyning is based on the trigometric identity:

$$\sin\theta\sin\varphi = \frac{1}{2}\cos(\theta - \varphi) - \frac{1}{2}\cos(\theta + \varphi)$$

The product on the left hand side represents the multiplication ("mixing") of a sine wave with another sine wave. The right hand side shows that the resulting signal is the difference of two sinusoidal terms, one at the sum of the two original frequencies, and one at the difference, which can be considered to be separate signals.

Using this trigonometric identity, the result of multiplying two sine wave signals, $\sin(2\pi f_1 t)$ and $\sin(2\pi f_2 t)$ can be calculated:

$$\sin(2\pi f_1 t)\sin(2\pi f_2 t) = \frac{1}{2}\cos[2\pi(f_1 - f_2)t] - \frac{1}{2}\cos[2\pi(f_1 + f_2)t]$$

The result is the sum of two sinusoidal signals, one at the sum $f_1+f_2$ and one at the difference $f_1-f_2$ of the original frequencies Mixer The two signals are combined in a device called a mixer. It can be seen from the previous section that the ideal mixer would be a device that multiplies the two signals. Such devices, called analog multipliers, exist and are used as mixers at lower frequencies, but do not function well at the RF frequencies where heterodyning is usually used. However, almost any non-linear electronic component will also multiply signals applied to it, producing heterodyne frequencies in its output, so these are most often used as mixers. A non-linear component is one in which the output current or voltage is a non-linear function of its input. Most circuit elements in communications circuits are designed to be linear. This means they obey the superposition principle; if $F(v)$ is the output of a linear element with an input of v:

$$F(v_1+v_2)=F(v_1)+F(v_2)$$

If two sine wave signals are applied to a linear device, the output is the sum of the outputs when the two signals are applied separately, with no product terms. So the function F must be non-linear. The only drawback to using a non-linear component rather than a multiplier is that, in addition to the sum and difference frequencies, it produces other unwanted frequency components called harmonics, which must be filtered from the output to leave the desired heterodyne frequency.

Examples of non-linear components that are used as mixers are vacuum tubes and transistors biased near cut-off (class C), and diodes. Ferromagnetic core inductors driven into saturation can also be used. In non-linear optics, crystals that have non-linear characteristics are used to mix laser light beams to create heterodynes at optical frequencies.

Output of a Mixer

To demonstrate mathematically how a non-linear component can multiply signals and generate heterodyne frequencies, the non-linear function F can be expanded in a power series (MacLaurin series):

$$F(v)=\alpha_1 v+\alpha_2 v^2+\alpha_3 v^3+$$

To simplify the math, the higher order terms above $\alpha_2$ will be indicated by an ellipsis ("...") and only the first terms will be shown. Applying the two sine waves at frequencies $\omega_1=2\pi f_1$ and $\omega_2=2\pi f_2$ to this device:

$$v_{out}=F(A_1 \sin \omega_1 t+A_2 \sin \omega_2 t)$$

$$v_{out}=\alpha_1(A_1 \sin \omega_1 t+A_2 \sin \omega_2 t)+\alpha_2(A_1 \sin \omega_1 t+A_2 \sin \omega_2 t)^2+$$

$$v_{out}=\alpha_1(A_1 \sin \omega_1 t+A_2 \sin \omega_2 t)+\alpha_2(A_1^2 \sin^2 \omega_1 t+ 2A_1 A_2 \sin \omega_1 t \sin \omega_2 t+A_2^2 \sin^2 \omega_2 t)+$$

The second term above contains a product of the two sine waves. Simplifying with trigonometric identities:

$$v_{out} = \alpha_1(A_1 \sin\omega_1 t + A_2 \sin\omega_2 t) + \alpha_2\left(\frac{A_1^2}{2}[1 - \cos 2\omega_1 t] + A_1 A_2[\cos(\omega_1 t - \omega_2 t) - \cos(\omega_1 t + \omega_2 t)] + \frac{A_2^2}{2}[1 - \cos 2\omega_2 t]\right) + \ldots$$

$$v_{out} = \alpha_2 A_1 A_2 \cos(\omega_1 - \omega_2)t - \alpha_2 A_1 A_2 \cos(\omega_1 + \omega_2)t + \ldots$$

So the output contains sinusoidal terms with frequencies at the sum $\omega_1+\omega_2$ and difference $\omega_1-\omega_2$ of the two original frequencies. It also contains terms at the original frequencies and at multiples of the original frequencies $2\omega_1$, $2\omega_2$, $3\omega_1$, $3\omega_2$, etc.; the latter are called harmonics. These unwanted frequencies, along with the unwanted heterodyne frequency, must be filtered out of the mixer output to leave the desired heterodyne.

The "multiplier" in a radio can be a tube or transistor, while in our DPOAE case we simply calculate the product sample by sample.

A special case of this is to "mix down" the signal to zero, or "base band". Let our DPOAE be at 2 kHz. We would have a "local oscillator" exactly at 2 kHz, and multiply this sine wave (sample by sample) with the incoming microphone signal, containing the DPOAE that we look for.

This is done with the original local oscillator signal, and a version that is phase shifted by 90°. This procedure is called quadrature demodulation, but a similar principle is also the core of the Fourier transform.

In this case, the 2 kHz DPOAE signal would be "mixed down" to frequency 0, which means DC. To make this work for all possible phase shifts between our local oscillator and the DPOAE signal, we need the 90° shifted version as well, and end up with the so-called I and Q signals, which in an FFT would be called real and imaginary part. This vector signal is then sliced into frames of, say, 2048 samples, windowed to avoid cutting effects, and averaged with some artefact rejection mechanism (I use "weighted averaging").

The advantage is, that this detection will also work if the stimulus frequencies, and with it the DPOAE frequency, are not multiples of the frame rate. They can even change over time (frequency modulation). The only important thing is that we must know the DPOAE frequency at all times, which we do since it is always following 2*f1−f2. Frequency shifting must also be done in a way that the DPOAE phase does not "run away" too far during testing. This somewhat limits modulation depth, but the exact selection on how to modulate f1 and f2 seems to influence this phase error, which can therefore be reduced to acceptable values.

In summary, the algorithm needs to support a frequency modulation of the stimuli while still detecting the resulting DPOAE, which will in most cases also be frequency modulated. Common FFT-based algorithms would not do so.

In one version of the PC software, it generates plots for longer term monitoring of OAEs, for monitoring ototoxic effects as well as recovery from ear attacks etc. The scale would be in hours, days or weeks, as needed, and plot the DPOAE amplitude of certain frequencies, probably in a different color for each frequency. This enables one to easily see which frequencies are going up or down in amplitude during treatment or recovery.

It is a different way of plotting things that already exist for use with the FMDPOAE to provide better reproducibility, because of the reduced effect of the fine structure.

This application of the method usually provides better accuracy in longer term monitoring of OAE amplitudes amid ototoxic treatment, recovery after surgery or other incidents. This is because the fine structure can change during recovery or damage of the inner ear, impacting outcomes of the single measurements. This would in turn corrupt the comparison of DPOAE between tests.

Figure 9:
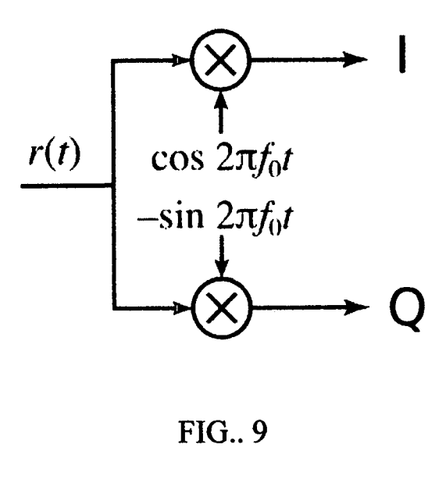
FIG. 9 is a circuit control graph.

FIG. 9 is a circuit control graph employed by the present invention.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method for measuring distortion product otoacoustic emissions (DPOAE) by means of frequency modulated stimuli to reduce or suppress DPOAE fine structure generation comprising:
   a. exposing a test subject's cochlea to an incoming signal from a signal generator comprised of at least two primary tones $f_1$ and $f_2$ to elicit DPOAE responses, of which at least one primary tone is continuously modulated in frequency to elicit DPOAE responses and reduce or suppress the effect of DPOAE fine structure during testing to provide better accuracy and reproducibility of such measurements, wherein $f_1=f_{1BASE}+f_1(t)$; $f_2=f_{2BASE}+f_2(t)$, and $f_{DPOAE}=f_{DOPAE\_BASE}+f(t)$ with $f(t)=2*f_1(t)-f_2(t)$,
   b. recording with at least one microphone DPOAE signals, at known, frequency $f_{DPOAE}$ in response to a frequency modulated signal,
   c. applying averaging or equivalent scheme with a processor and software to reduce noise in recorded DPOAE signals, and
   d. applying statistical methods via processor software to recorded DPOAE signals to determine if a valid response was detected and/or estimate DPOAE sound levels.

2. A method for measuring DPOAE according to claim 1, wherein the method is used for newborn hearing screening.

3. A method for measuring DPOAE according to claim 1, wherein the method is used for diagnostic DPOAE measurements.

4. A method for measuring DPOAE according to claim 1, wherein the method is used for estimating hearing threshold and I or calculation of hearing aid fitting parameters.

5. A method for measuring DPOAE according to claim 1, wherein the method is used for long-term monitoring of DPOAE by comparing measurements taken over hours to weeks, to be used for medical recovery processes or for monitoring ototoxic effects.

6. A method for measuring DPOAE according to claim 1, wherein frequency modulated primary tones are used not only for suppression of fine structure, but in conjunction with performance of other hearing testing, measurements, and analysis.

7. A method for measuring DPOAE according to claim 6, wherein the method is used for measuring contralateral suppression of DPOAE.

8. A method for measuring DPOAE according to claim 1, wherein statistical method to reject environmental noise artifacts comprises weighted averaging.

9. A method for measuring DPOAE according to claim 1, wherein quadrature demodulation is used to detect DPOAE signals.

10. A method for measuring DPOAE according to claim 9, including:
    a. calculating I and Q components of quadrature signals by multiplying incoming (raw or pre-filtered) microphone input signals with appropriate sine and cosine functions,
    b. windowing and framing I and Q data independently,
    c. averaging I and Q signals with optional weighting, and
    d. statistically evaluating averaged I/Q vectors to detect a statistically significant DPOAE signal and/or estimate its amplitude.

11. An apparatus for measuring measuring distortion product otoacoustic emissions (DPOAE) by means of frequency modulated stimuli to reduce or suppress DPOAE fine structure generation comprising:
    a. loudspeakers configured to expose cochlea of a test subject to a series of loudspeaker input signals, each input signal comprised of only two primary tones $f_1$ and $f_2$ to elicit DPOAE responses, wherein $f_1=f_{1BASE}+f_1(t)$; $f_2=f_{2BASE}+f_2(t)$, $f_{DPOAE}=f_{DOPAE\_BASE}+f(t)$ with $f(t)=2*f_1(t)-f_2(t)$,
    b. signal generators configured to generate the loudspeaker input signals and frequency-modulating at least one of the primary tones of each loudspeaker input signal continuously during testing with modulation function(s) wherein the primary tones of the incoming signals are selected over a frequency range to generate DPOAE signals and reduce or suppress generation of DPOAE fine structure during testing to provide better accuracy and reproducibility of such measurements,
    c. microphone(s) configured to record DPOAE signals, at known, possibly variable, frequency $f_{DPOAE}$,
    d. a processor and software configured to apply averaging or equivalent scheme to reduce noise in recordings, and
    e. software configured to apply statistical methods to DPOAE recordings to determine if a valid response was detected and/or estimate DPOAE sound levels.

12. A method for measuring distortion product otoacoustic emissions (DPOAE) by means of frequency modulated stimuli to reduce or suppress DPOAE fine structure generation comprising:
    a. exposing a test subject's cochlea to an incoming signal from a signal generator comprised of only two primary tones $f_1$ and $f_2$ to elicit DPOAE responses, wherein $f_1=f_{1BASE}+f_1(t)$; $f_2=f_{2BASE}+f_2(t)$, $f_{DPOAE}=f_{DOPAE\_BASE}+f(t)$ with $f(t)=2*f_1(t)-f_2(t)$, of which at least one primary tone is continuously modulated in frequency to elicit DPOAE responses and reduce or suppress DPOAE fine structure generation during testing to provide better accuracy and reproducibility of such measurements,
b. recording with at least one microphone DPOAE signals, at known, possibly variable, frequency $f_{DPOAE}$,
c. applying averaging or equivalent scheme with a processor and software to reduce noise in recorded DPOAE signals, and
d. applying statistical methods via processor software to recorded DPOAE signals to determine if a valid response was detected and/or estimate DPOAE sound levels.

13. A method for measuring DPOAE according to claim 1, wherein the method is used for newborn hearing screening.

14. A method for measuring DPOAE according to claim 12, wherein the method is used for diagnostic DPOAE measurements.

15. A method for measuring DPOAE according to claim 12, wherein the method is used for estimating hearing threshold and I or calculation of hearing aid fitting parameters.

16. A method for measuring DPOAE according to claim 12, wherein the method is used for long-term monitoring of DPOAE by comparing measurements taken over hours to weeks, to be used for medical recovery processes or for monitoring ototoxic effects.

17. A method for measuring DPOAE according to claim 12, wherein frequency modulated primary tones are used not only for suppression of fine structure, but in conjunction with performance of other hearing testing, measurements, and analysis.

18. A method for measuring DPOAE according to claim 17, wherein the method is used for measuring contralateral suppression of DPOAE.

19. A method for measuring DPOAE according to claim 12, wherein statistical method to reject environmental noise artifacts comprises weighted averaging.

20. A method for measuring DPOAE according to claim 12, wherein quadrature demodulation is used to detect DPOAE signals.

21. A method for measuring DPOAE according to claim 20, including:
a. calculating I and Q components of quadrature signals by multiplying incoming (raw or pre-filtered) microphone input signals with appropriate sine and cosine functions,
b. windowing and framing I and Q data independently,
c. averaging I and Q signals with optional weighting, and
d. statistically evaluating averaged I/Q vectors to detect a statistically significant DPOAE signal and/or estimate its amplitude.

* * * * *